(12) United States Patent
Kim et al.

(10) Patent No.: US 7,407,673 B2
(45) Date of Patent: Aug. 5, 2008

(54) RADIOACTIVE MAGNETIC FLUIDS FOR TREATMENT OR DIAGNOSIS OF CANCER, PROCESS FOR PREPARING THEM AND USE THEREOF

(75) Inventors: Chong-Oh Kim, Doryong-dong 381-14, Yuseong-gu, Daejeon (KR) 305-340; Jong-Hee Kim, Daejeon (KR); Yuqiang Huang, Daejeon (KR); Sang-Im Park, Daejeon (KR)

(73) Assignee: Chong-Oh Kim, Daejeon (KR)

( * ) Notice: Subject to any disclaimer, the term of this patent is extended or adjusted under 35 U.S.C. 154(b) by 826 days.

(21) Appl. No.: 10/635,615

(22) Filed: Aug. 7, 2003

(65) Prior Publication Data

US 2005/0019257 A1 Jan. 27, 2005

(30) Foreign Application Priority Data

Jul. 11, 2003 (KR) ...................... 10-2003-0047219

(51) Int. Cl.
*A01N 59/20* (2006.01)
(52) U.S. Cl. ...................... 424/630; 424/646; 424/647; 424/648
(58) Field of Classification Search ........................ None
See application file for complete search history.

(56) References Cited

U.S. PATENT DOCUMENTS

| 4,957,481 | A | 9/1990 | Gatenby |
| 5,921,244 | A | 7/1999 | Chen et al. |
| 7,138,103 | B2 | 11/2006 | Goldenberg et al. |
| 2004/0248856 | A1* | 12/2004 | Lanza et al. ................. 514/124 |
| 2005/0085417 | A1* | 4/2005 | Wickstrom et al. ............ 514/12 |
| 2006/0286379 | A1* | 12/2006 | Gao ............................ 428/403 |

OTHER PUBLICATIONS

Sincai et al in Journal of Magnetism and Magnetic Materials 225 (2001) 235-240☐☐.*
Sieben et al in Journal of Magnetism and Magnetic Materials 225 (2001) 175-179.*
Kuznetsov et al in Journal of Magnetism and Magnetic Materials 194 (1999) 22-30☐☐.*
Kwon et al in Korean Journal of Materials Research vol. 12 (3) 2002 pp. 215 (English translation prepared by the USPTO).*
Urs Hafeli et al., "Radiolabeling of Magnetic Particles with Rhenium-188 for Cancer Therapy", Journal of Magnetism and Magnetic Materials, vol. 225, pp. 73-78 (2001).
Ch. Alexiou et al., "Magnetic Drug Targeting: Biodistribution and Dependency on Magnetic Field Strength", Journal of Magnetism and Magnetic Materials, vol. 252, pp. 363-366 (2002).
Yuqiang Huang et al., "Preparation of nanometric $Cu_xFe_{1-x}OFe_2O_3$ for Treatment of Tumor", Journal of Applied Physics, vol. 93, No. 10, pp. 8444-8446 (2003).

* cited by examiner

*Primary Examiner*—Michael G. Hartley
*Assistant Examiner*—Eric E Silverman
(74) *Attorney, Agent, or Firm*—Greenblum & Bernstein, P.L.C.

(57) ABSTRACT

The present invention relates to radioactive magnetic fluids, process for preparing them and use thereof. Particularly, the present invention relates to the radioactive magnetic fluids for treatment or diagnosis of cancer, process for preparing them and use thereof.

The radioactive magnetic fluids of the present invention include the component of $Cu^{2+}$ which radiates a β-ray and γ-ray. The β radiation can effectively kill the tumor cells. Since the γ radiation are easily imaged with γ-camera, the magnetic fluids can be gathered to the treatment site with the radiograph under external magnetic field. Therefore, the radioactive magnetic fluids of the present invention can be used for treatment of cancer with minimal side effects. Also, the tightly bonded decanoic acid and nonanoic acid layer of the present invention not only increase particle-particle repulsion but also take hydrophilicity, to disperse homogeneously and stably the magnetic nanoparticles in water. Also, carboxylic acid of the surfactant is exposed to outside, to prevent the magnetic nanoparticles from being oxidized by air.

Therefore, the radioactive magnetic fluids can be used as therapeutic drug or diagnostic reagent for cancer.

8 Claims, 6 Drawing Sheets

RADIOACTIVE MAGNETIC FLUIDS FOR TREATMENT OR DIAGNOSIS OF CANCER, PROCESS FOR PREPARING THEM AND USE THEREOF

TECHNICAL FIELD

The present invention relates to radioactive magnetic fluids, process for preparing them and use thereof. Particularly, the present invention relates to the radioactive magnetic fluids for treatment or diagnosis of cancer, process for preparing them and use thereof.

BACKGROUND OF THE INVENTION

Cancer is a significant problem in human health all over the world. At present, there are a number of methods and techniques for the treatment of cancer. A safe and effective cancer treatment has been the goal of investigators for a substantial period time. A technique for the successful cancer treatment must ultimately differentiate cancer cells from normal cells and must selectively weaken or kill only the cancer cells without affecting the normal cells. Some cancers such as eye cancer and liver cancer cannot be completely treated by a surgical operation.

Chemical therapy, radiate therapy and surgical operation are developed for the treatment of cancer.

In chemical therapy, a chemical material is administered to a body, which kills the cancer cell.

In surgical operation, the affected part of cancer is removed or dressed.

In radiate therapy, the radioactive element which radiates β(beta)-ray is used for treatment of cancer. The radiate therapy is divided into outer and inner radiate therapys. Outer radiate therapy is to kill the cancer cells by the β-ray radiated from outside. However, the disadvantage of outer radiate therapy is that the treatment efficiency is low and the side effect is too large because the radiation kills the cancer cell during treatment and at the same time destroys a lot of normal cells as well. Inner radiate therapy is to inject radioactive magnetic fluids into the body, and to kill the cancer cell by the β-ray radiated from the radioactive magnetic fluids under external magnetic field.

Particularly, in the inner radiate therapy, magnetic nanoparticles prepared with elements emitting the β-ray are coated with the surfactants to form the magnetic fluids which are injected into the body. Under external magnetic field, the β-ray radiated from the magnetic fluids is positioned around the affected part to kill the tumor cells.

The magnetic fluids used in inner radiate therapy is magnetic colloidal liquid prepared by the steps: 1) coating the magnetic powder with various surfactants, in which the magnetic powder is magnetic oxides such as $MO \cdot Fe_2O_3$ (M: metal cation of 2+) with a mean size of 100 Å; and 2) dispersing homogeneously and stably the said coated particles into a liquid.

The magnetic fluids as colloidal particles in a suspension are not agglomerated or precipitated by gravity or magnetic force.

U.S. Pat. No. 5,921,244 suggests the process of magnetic fluids containing the particles coated with photoreactive agent. However, it is restricted within the purpose of drug therapy by a light source using a magnet inserted into the body. Also, U.S. Pat. No. 4,957,481 deals with the effective amount and direct injection of a photosensitive compound into tumor, and the application and activation of light source.

DISCLOSURE OF THE INVENTION

It is an object of the present invention to provide the radioactive magnetic fluids for treatment or diagnosis of cancer.

It is another object of the present invention to provide the process for preparing the radioactive magnetic fluids.

It is another object of the present invention to provide the use of the radioactive magnetic fluids.

BRIEF DESCRIPTION OF THE DRAWINGS

The above and other objects, features and advantages of the present invention will be more clearly understood from the following detailed description taken in conjunction with the accompanying drawings, in which.

BEST MODE FOR CARRYING OUT THE INVENTION

Figure 1:
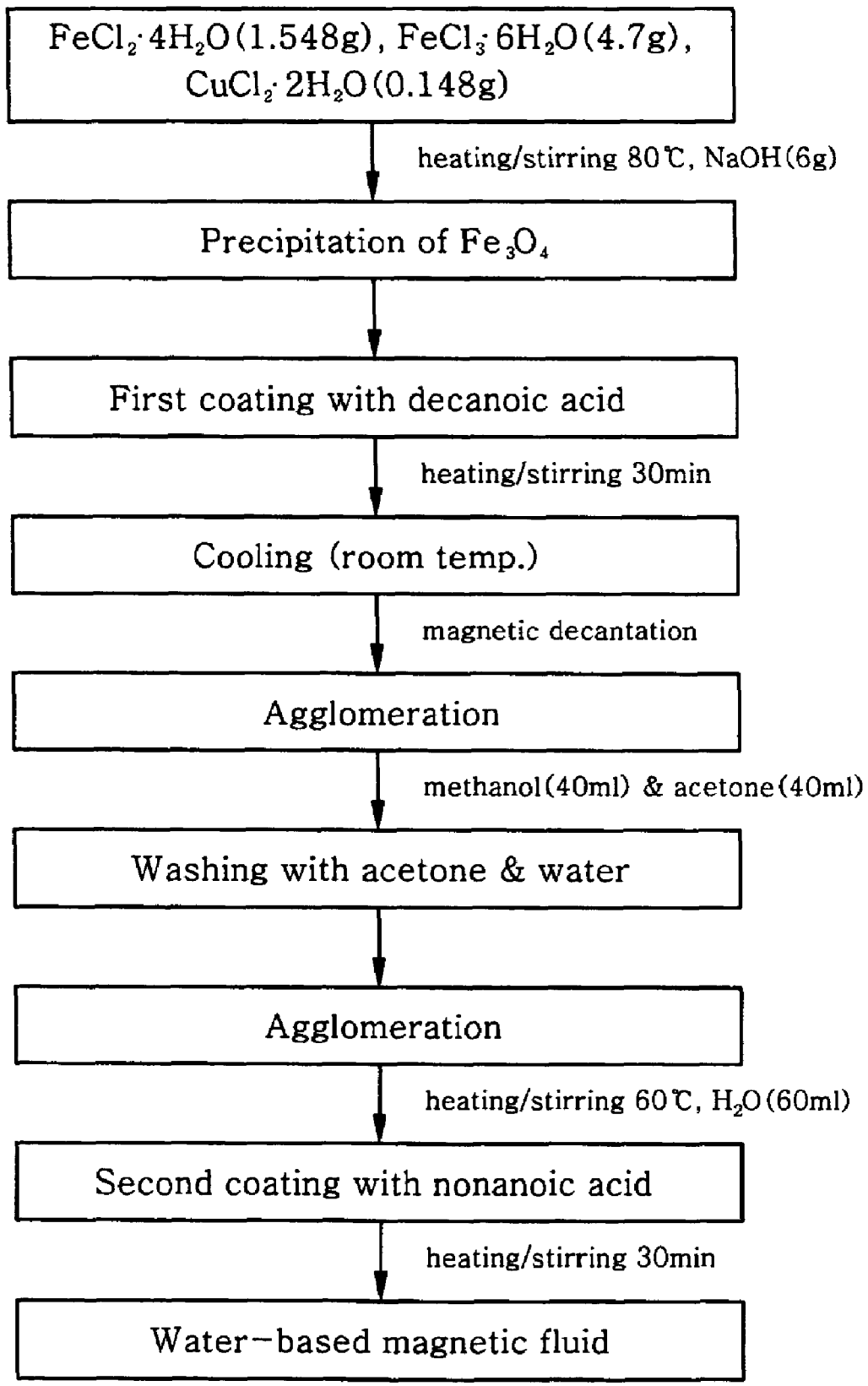
FIG. 1 is a flow chart diagram of the steps for preparation of the radioactive magnetic fluids of the present invention.

The present invention provides radioactive magnetic fluids for treatment or diagnosis of cancer. Particularly, the present invention provides radioactive magnetic fluids comprising: magnetic nanoparticles; and surfactants coated onto the magnetic nanoparticles, wherein the radioactive copper is a component part of the magnetic nanoparticles.

Preferably, the present invention provides the radioactive magnetic fluids, wherein the magnetic nanoparticles are obtained with synthesis of $Cu_xFe_{1-x}O \cdot Fe_2O_3$ by a chemical reaction of the $Cu^{2+}$ component with the components of $Fe^{2+}$ and $Fe^{3+}$.

More preferably, the present invention provides the radioactive magnetic fluids, wherein the surfactants comprise the first surfactant coated onto the surface of the magnetic nanoparticles, the first surfactant being decanoic acid, and the second surfactant coated onto the first-coated magnetic nanoparticles, the second surfactant being nonanoic acid.

Wherein, x value of $Cu_xFe_{1-x}O \cdot Fe_2O_3$ in a chemical composition of the magnetic nanoparticles is between 0.1 and 0.4.

The magnetic nanoparticles of $Cu_xFe_{1-x}O \cdot Fe_2O_3$ are prepared by a one-step method, wherein $Cu^{2+}$ is precipitated simultaneously with $Fe^{2+}$ and $Fe^{3+}$. Particularly, the colloidal particles of $Fe_3O_4$ are prepared by coprecipitating the solutions of $Fe^{2+}$ and $Fe^{3+}$. Thereafter, $Cu^{2+}$ is incorporated into the, magnetite crystal by substituting $Fe^{2+}$ from the $Fe_3O_4$.

The copper element is a radionuclide emitting the β-ray with a energy of 0.577 MeV and a half time of 61.83 h. The said β-ray penetrates through several millimeters of the body tissue with a short effective range. Therefore, the radioactive magnetic fluids of the present invention can be used for treatment of cancer with minimal damage to normal tissue.

Also, the copper element radiates γ(gamma)-ray of 150 keV close to the energy of 99 mTc which is often used in tumor diagnosis[Urs Hafeli, Gayle Pauer, Sarah Failing, Gilles Tapolsky, "Radiolabeling of magnetic particles with rhenium-188 for cancer therapy", *Journal of Magnetism and Magnetic materials*, 255, 2001, 73-78]. Since the said γ radiation is easily imaged with γ-camera, the magnetic fluid can be gathered to the treatment site with the radiograph under external magnetic field[Ch. Alexiou, A. Schmidt, R. Klein, P. Hulin, Ch. Bergemann, W. Arnold, "Magnetic drug targeting: biodistribution and dependency on magnetic field strength", *Journal of Magnetism and Magnetic Materials*, 252, 2002, 363-366].

Therefore, the radioactive magnetic fluids of the present invention which are injected into the body through artery can be immobilized at the affected part by imaging with γ-camera under external magnetic field. The magnetic field system gathers the magnetic fluids to create an optimum radiation intensity developed on the desired part of the organism, keeping the total injected dose low. The radioactive magnetic fluids of the present invention kill the tumor cells with little damage to the normal tissue following by minimizing side effects. The radioactive magnetic fluids can be also positioned in the fine organism such as liver and internal organs, to treat the affected part.

Atomic radius, electronegativity and valence of the Cu element are quite similar to those of the Fe element. Since $Cu^{2+}$ can substitute $Fe^{2+}$ from the $Fe_3O_4$ according to Hume-Rothery rule, the $Cu^{2+}$ substitutionally bonded in the oxide crystal. Therefore, the radioactive magnetic fluids can be stably delivered to the affected part, to become both carrier and drug to be bifunctional agent.

Generally, in radiate therapy, the dosage of radioactivity for the treatment of cancer keeps 40~100 MBq (Bq means one atom disintegration per second). It indicates that the mass of radioactive $Cu^{2+}$ disintegrated per second is $4.89~12.22 \times 10^{-11}$. Although only a few $Fe^{2+}$ from the said $Fe_3O_4$ are substituted by $Cu^{2+}$ the prepared magnetic fluids can have both desirable radioactivity and sufficient magnetization.

The decanoic acid or nonanoic acid acts as surfactants. Particularly, a functional group of the acid is adsorbed onto the surface of the magnetic nanoparticles prepared by chemical coprecipitation, to form a monomolecular layer around the said particles. The tightly bonded decanoic acid or nonanoic acid layer does not only increase particle-particle repulsion but also takes hydrophobicity or hydrophilicity, to disperse homogeneously and stably the magnetic nanoparticles in the liquid medium. Also, carboxylic acid of the surfactant is exposed to the outside, to prevent the magnetic nanoparticles from being oxidized by air.

Since the decanoic acid or nonanoic acid is biodegradable fatty acid, the biodegradable magnetic particles coated with the fatty acid can eventually be incorporated into the subject's hemoglobin. Thus, the magnetic particles of the present invention are well-suited for in vivo use.

Also, the present invention provides the process for preparing the radioactive magnetic fluids. Particularly, the process of the present invention comprises:

1) preparing the magnetic nanoparticles of $Cu_xFe_{1-x}O\cdot Fe_2O_3$ by coprecipitating components of $Fe^{2+}$ and $Fe^{3+}$ with a component of $Cu^{2+}$ under the presence of precipitator (step 1);

2) first coating the magnetic nanoparticles with decanoic acid (step 2); and 3) second coating the first-coated magnetic nanoparticles with nonanoic acid (step 3).

(Step 1)

As shown in the scheme 1, the magnetic nanoparticles of $Cu_xFe_{1-x}O\cdot Fe_2O_3$ is prepared by coprecipitating the components of $Fe^{2+}$ and $Fe^{3+}$ together with the component of $Cu^{2+}$ under the presence of precipitator.

<Scheme 1>

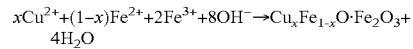

The coprecipitation is the process that the mixed solution of $Fe^{2+}$, $Fe^{3+}$ and $Cu^{2+}$ is heated and stirred at the temperature of 80° C. In the said process, $Fe_3O_4$ is synthesized from the solutions of $Fe^{2+}$ and $Fe^{3+}$, and $Cu^{2+}$ is incorporated into the crystal of magnetite by substituting $Fe^{2+}$ from the said $Fe_3O_4$.

Also, the precipitator is preferable sodium hydroxide. In the case of ammonia water, the excess reacts with $Cu(OH)_2$ to produce the chelate compound of $[Cu(NH_3)_4]^{2+}$. Therefore, the excess ammonia must be removed in the washing process. The mixture is vigrously agitated in order to restrict the growth of particles.

Also, the mole ratio of $(Cu^{2+}+Fe^{2+})$ to $Fe^{3+}$ is within range of $(1.1~1.4):2$.

The starting materials for $Fe^{2+}$ and $Fe^{3+}$ are preferable iron(II) chloride tetrahydrate ($FeCl_2 \cdot 4H_2O$) and iron(III) chloride hexahydrate ($FeCl_3 \cdot 6H_2O$), respectively. And the starting material for $Cu^{2+}$ is preferable copper(II) chloride dehydrate ($CuCl_2 \cdot 2H_2O$). In case of the above, the reaction of the step 1 is shown in scheme 2.

<Scheme 2>

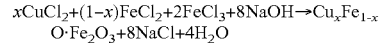

(wherein, x value of $Cu_xFe_{1-x}O\cdot Fe_2O_3$ in a chemical composition of magnetic nanoparticles is between 0.1 and 0.4.)

The magnetic nanoparticles are prepared with the mean size of about 10 nanometers by the said chemical coprecipitation.

(Step 2)

The magnetic nanoparticles prepared in the above step 1 are first coated with decanoic acid.

Particularly, decanoic acid is added to the said magnetic nanoparticles prepared in the above step 1, thereafter the resulting mixture is stirred for 30 min and heated to 80° C. Thus, decanoic acid is chemisorbed on the surface of the magnetic nanoparticles.

(Step 3)

The first-coated magnetic nanoparticles prepared in the above step 2 are secondly coated with nonanoic acid.

Particularly, nonanoic acid is added to the said first-coated magnetic nanoparticles prepared in the above step 2, thereafter the resulting mixture is stirred for 30 min and heated to 60° C. Thus, water-based magnetic fluids are prepared by immobilizing nonanoic acid.

FIG. 1 is a flow chart diagram of the process for preparing the radioactive magnetic fluids according to the present invention. As shown in the FIG. 1, $CuCl_2 \cdot 2H_2O$ (0.148 g) and $FeCl_2 \cdot 4H_2O$ (1.548 g) and $FeCl_3 \cdot 6H_2O$ (4.7 g) are dissolved in water. The mixed solution is stirred and heated to 80° C. The nano-sized particles are prepared with the addition of NaOH to the solution. Decanoic acid is used as the first surfactant, which is dissolved in solvent. The resulting liquid is added to the said nano-sized particles. The mixture is stirred and heated, for the said nano-sized particles to be first coated with decanoic acid, thereafter the mixture is cooled to the room temperature, for the coated decanoic acid not to break away from the magnetic nanoparticles. The excess decanoic acid is removed by washing with acetone. Subsequently, the remaining acetone is removed by washing with water.

Nonanoic acid as the second surfactant is used with a small amount of NaOH. The resulting liquid is added to the said first-coated particles. The mixture is stirred and heated for the first-coated particles to be secondly coated with nonanoic acid.

Figure 2:
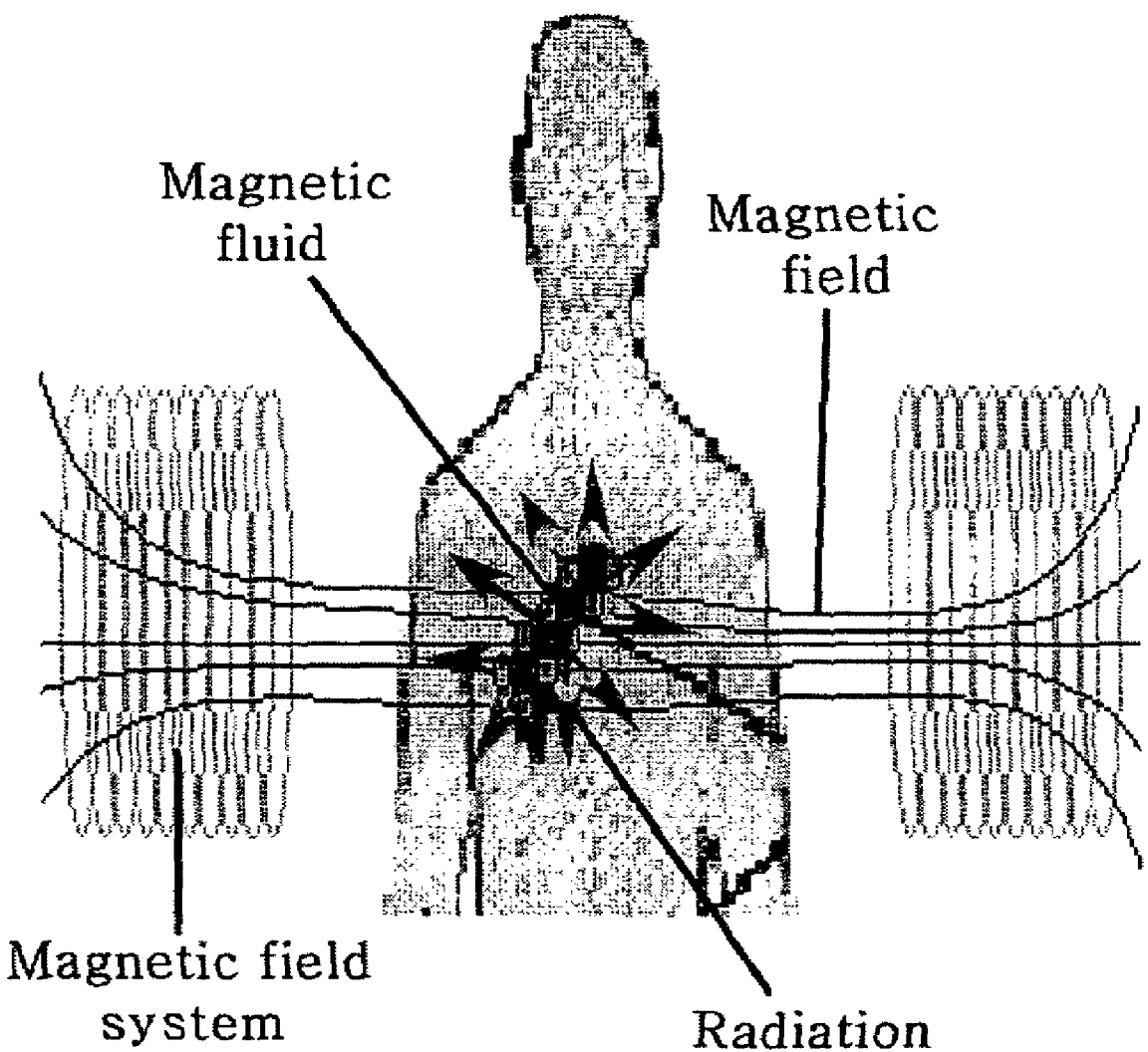
FIG. 2 shows a principle of treatment on a human body by radiate therapy using the radioactive magnetic fluids of the present invention.

FIG. 2 shows a principle of treatment on a human body by radiate therapy using the radioactive magnetic fluid of this invention.

The radioactive magnetic fluids are injected into the body through artery. As shown in FIG. 2, the radioactive magnetic fluids are immobilized at the affected part by an external magnetic field, radiating β-ray and γ-ray for half time. The radiated β-ray can treat the cancer by killing the tumor cell. Since the radiated γ-ray is easily imaged with γ-camera, the magnetic fluids can be gathered to the treatment site with the radiograph under external magnetic field.

Therefore, the radioactive magnetic fluids of the present invention can be used for treatment or diagnosis of cancer as therapeutic drug or diagnostic reagent for cancer.

Also, the radioactive magnetic fluids according to the present invention can be applied in biomedical application such as drug delivery and cell separation. In case of drug delivery, for example, drug can be adsorbed onto the surface of the radioactive magnetic fluids. Thereafter, the said radioactive magnetic fluids can be delivered to the affected part using an external magnetic field system.

The present invention will be explained in more detail with reference to the following examples in conjunction with the accompanying drawings. However, the following examples are provided only to illustrate the present invention, and the present invention is not limited to them.

EXAMPLE 1

$FeCl_2 \cdot 4H_2O$ 1.548 g, $FeCl_3 \cdot 6H_2O$ 4.7 g and $CuCl_2 \cdot 2H_2O$ 0.148 g were dissolved in 80 ml of distilled water. The mixed solution was poured into a flask with three ports, was heated to 80° C. and was stirred at 300 rpm. About 2 g of magnetic nanoparticles was prepared by adding aqueous sodium hydroxide 10 ml (sodium hydroxide 6 g contained) to the mixed solution and also stirring.

2.4 g of decanoic acid was dissolved in acetone 60 ml, to prepare the decanoic acid solution. The said decanoic acid solution was added to the said magnetic nanoparticles in six stages. The resulting mixture was stirred and heated, for the said magnetic nanoparticles to be first coated with decanoic acid, was cooled to the room temperature, and was washed with acetone and water.

Thereafter, 3 ml of nonanoic acid and 2 ml of $NH_4OH$ were added to the first-coated magnetic nanoparticles. The resulting mixture was stirred for 30 min and heated to 60° C., and was cooled to the room temperature, to prepare the radioactive water-based magnetic fluids.

EXPERIMENTAL EXAMPLE 1

Magnetization of the Radioactive Magnetic Fluids

Whether $Cu^{2+}$ substituted $Fe^{2+}$ of $Fe_3O_4$ was observed by X-ray diffraction of the magnetic nanoparticles prepared in the example 1.

Figure 3:
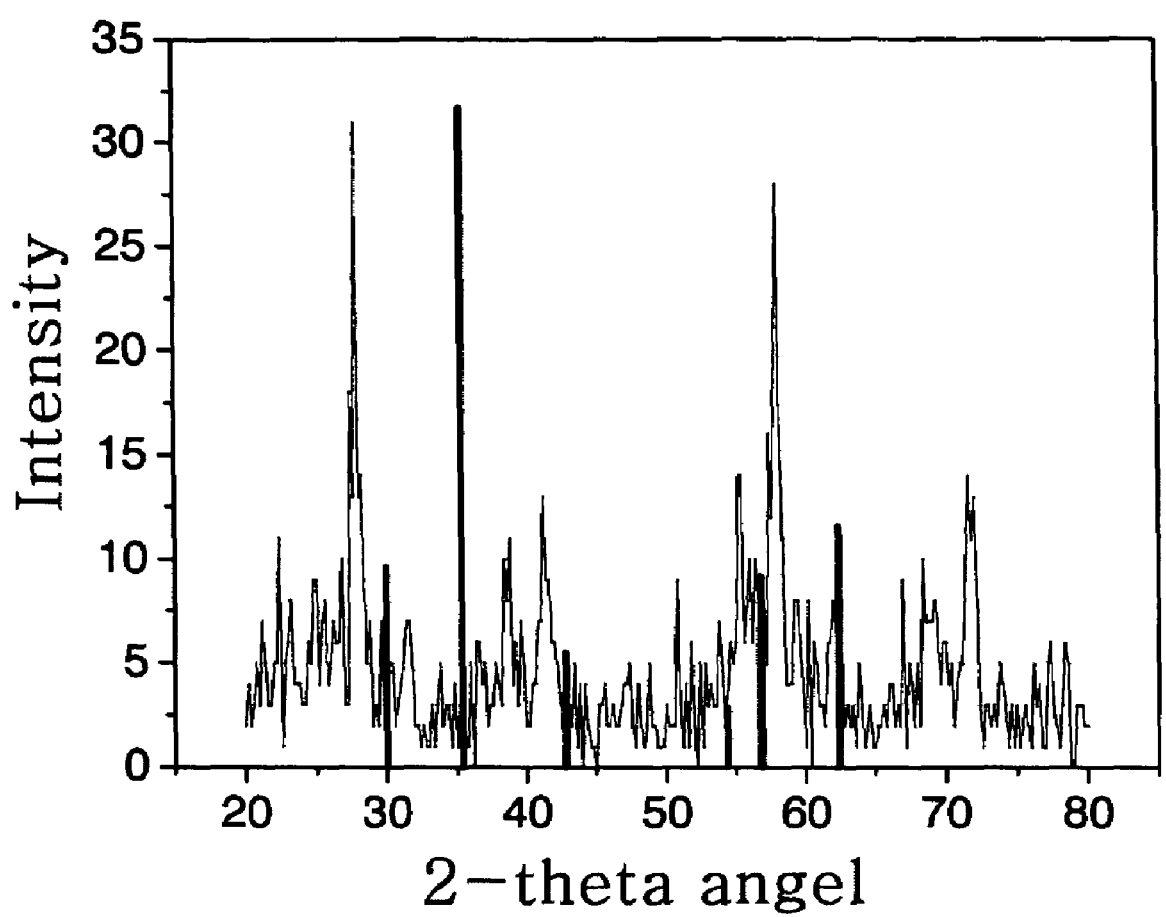
FIG. 3 shows a typical X-ray diffraction pattern for the nanoparticles of magnetite ($Fe_3O_4$) with a copper content of 10%.

The result is shown in FIG. 3.

In FIG. 3, the vertical bold lines are the standard diffraction pattern for magnetite ($Fe_3O_4$).

As shown in FIG. 3, intensity and position of the standard diffraction peaks were considerably changed by the incorporation of $Cu^{2+}$ into the magnetite. The result revealed that a ferromagnetic $Fe^{2+}$ of the magnetite was in part substituted by a diamagnetic $Cu^{2+}$. Particularly, ionic radius of $Cu^{2+}$ (0.069 nm) is smaller than that of $Fe^{2+}$ (0.076 nm). Therefore, positions of the diffraction peaks for the radioactive magnetic nanoparticles are shifted to the right due to the increase of diffraction angles from Bragg's law, compared with the standard diffraction pattern of magnetite.

EXPERIMENTAL EXAMPLE 2

Magnetization of the Radioactive Magnetic Nanoparticles with Different Contents of $Cu^{2+}$ Magnetization of the radioactive magnetic nanoparticles was measured with different contents of $Cu^{2+}$ by the following experiment.

The contents of $CuCl_2 \cdot 2H_2O$, $FeCl_3 \cdot 6H_2O$ and $FeCl_2 \cdot 4H_2O$ are represented in table 1. Particularly, with the constant quantity of 4.700 g for $FeCl_3 \cdot 6H_2O$, 0.148 g, 0.296 g, 0.445 g and 0.593 g of $CuCl_2 \cdot 2H_2O$ were added to 1.548 g, 1.376 g, 1.204 g and 1.032 g of $FeCl_2 \cdot 4H_2O$, respectively. According to the process of example 1, the magnetic nanoparticles of $Cu_xFe_{1-x}O \cdot Fe_2O_3$ were prepared with the above mixed compounds.

Using the magnetic nanoparticles prepared as samples, the value of x for $Cu_xFe_{1-x}O \cdot Fe_2O_3$ was measured by atomic absorption spectroscopy (AA). The results are also listed in table 1.

TABLE 1

| Content | $CuCl_2 \cdot 2H_2O$ | $FeCl_2 \cdot 4H_2O$ | $FeCl_3 \cdot 6H_2O$ | x value of $Cu_xFe_{1-x}O \cdot Fe_2O_3$ |
|---|---|---|---|---|
| Sample 1 | 0.148 | 1.548 | 4.7 | 0.1 |
| Sample 2 | 0.296 | 1.376 | 4.7 | 0.2 |
| Sample 3 | 0.445 | 1.204 | 4.7 | 0.3 |
| Sample 4 | 0.593 | 1.032 | 4.7 | 0.4 |

As shown in table 1, the x value of $Cu_xFe_{1-x}O \cdot Fe_2O_3$ for the magnetic nanoparticles became in turn 0.1, 0.2, 0.3 and 0.4 with increasing copper contents in the samples. Also, the magnetization of magnetic nanoparticles prepared with the above samples was measured using vibrating sample magnetometer (VSM).

Figure 4:
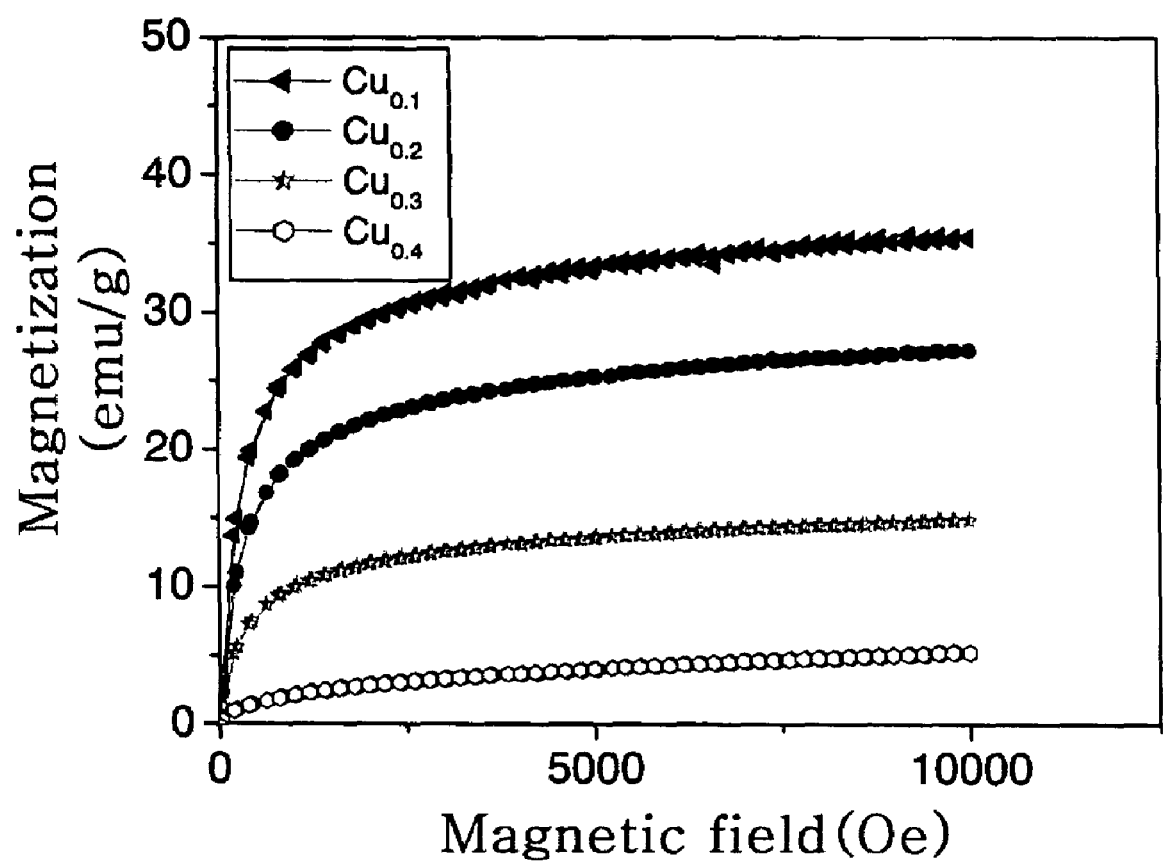
FIG. 4 shows magnetization curves for magnetic nanoparticles of $Cu_xFe_{1-x}O \cdot Fe_2O_3$ with different $Cu^{2+}$ contents.

The results are shown in FIG. 4, wherein $Cu_{0.1}$, $Cu_{0.2}$, $Cu_{0.3}$ and $Cu_{0.4}$ indicate the Cu fractions for $Cu_xFe_{1-x}O \cdot Fe_2O_3$ of magnetic nanoparticles.

As shown in FIG. 4, the magnetization of the magnetic nanoparticles decreased with increasing $Cu^{2+}$ contents. The reason is that the amount of the ferromagnetic phase decreases in the magnetic nanoparticles while the diamagnetic $Cu^{2+}$ substitutionally occupies the site of $Fe^{2+}$ in the crystal structure of $Fe_3O_4$.

EXPERIMENTAL EXAMPLE 3

Effect of Precipitator on Characteristic of Magnetic Fluids

Concentration of magnetic fluid, magnetization of magnetic nanoparticle and atomic fraction of copper about the magnetic nanoparticles prepared with different precipitators were observed by the following experiment.

Ammonia water or sodium hydroxide was used as precipitator, in the amount of 10 ml and 15 ml. According to the process of example 1, the magnetic nanoparticles of $Cu_xFe_{1-x}O \cdot Fe_2O_3$ were prepared.

Magnetization of the magnetic nanoparticles and atomic fraction of copper were measured by the process of experimental example 2. And concentration of the magnetic fluids was calculated.

Figure 5:
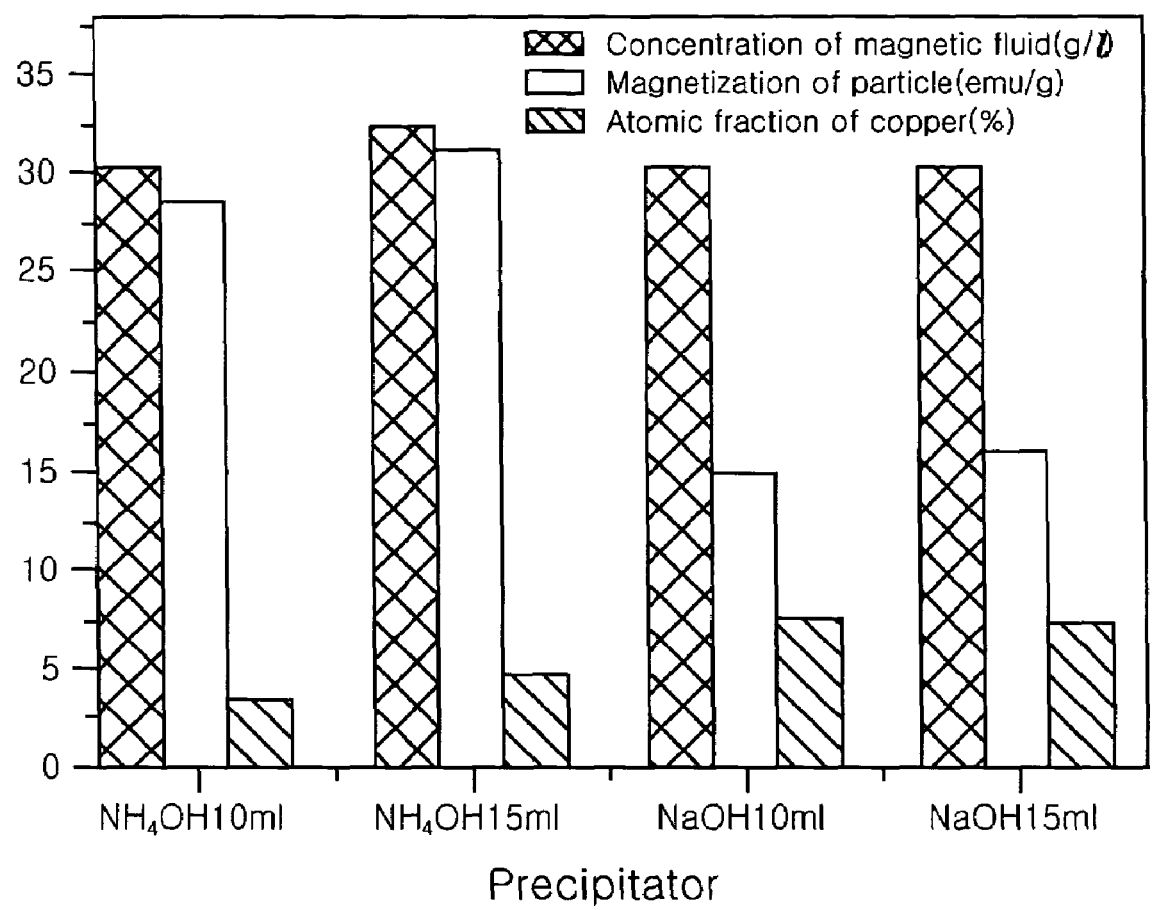
FIG. 5 shows concentration of magnetic fluids, magnetization of nanoparticles and atomic fraction of copper about the magnetic nanoparticles obtained with different precipitators.

The results are shown in FIG. 5.

As shown in FIG. 5, different kind of precipitators had little influence on the concentration of the magnetic fluids but had considerable influence on the magnetization of the magnetic fluids. Particularly, in the case using sodium hydroxide compared with ammonia water, the magnetization of the magnetic nanoparticles decreased while the content of the coprecipitated copper increased. This result obviously corresponds to the one of experimental example 2.

EXPERIMENTAL EXAMPLE 4

Effect of $(Cu^{2+}+Fe^{2+}):Fe^{3+}$ on Magnetization of Magnetic Particles

Magnetization of the magnetic nanoparticles was measured with different mole ratios of $(Cu^{2+}+Fe^{2+})$ to $Fe^{3+}$ by the following experiment. The above $(Cu^{2+}+Fe^{2+})$ means to be sum of $Cu^{2+}$ and $Fe^{2+}$ contents in the magnetic nanoparticles of $Cu_xFe_{1-x}O \cdot Fe_2O_3$ prepared in the present invention. The mole ratio of $(Cu^{2+}+Fe^{2+})$ to $Fe^{3+}$ is theoretically 1:2. The above ratio is suitable for the preparation of magnetic nanoparticles in inert gas. However, under the atmosphere, a good magnetization cannot be obtained with the above ratio, due to the oxidation by air.

According to the process of example 1, the magnetic nanoparticles were prepared with different mole ratios of $(Cu^{2+}+Fe^{2+})$ to $Fe^{3+}$. Based on the theoretical value 1:2, the mole ratios of $(Cu^{2+}+Fe^{2+})$ to $Fe^{3+}$ were below 1.0:2, 1.1:2, 1.2:2, 1.3:2, 1.4:2 and excess 1.4:2. The magnetization of the magnetic nanoparticles was measured by the process of experimental example 2.

Figure 6:
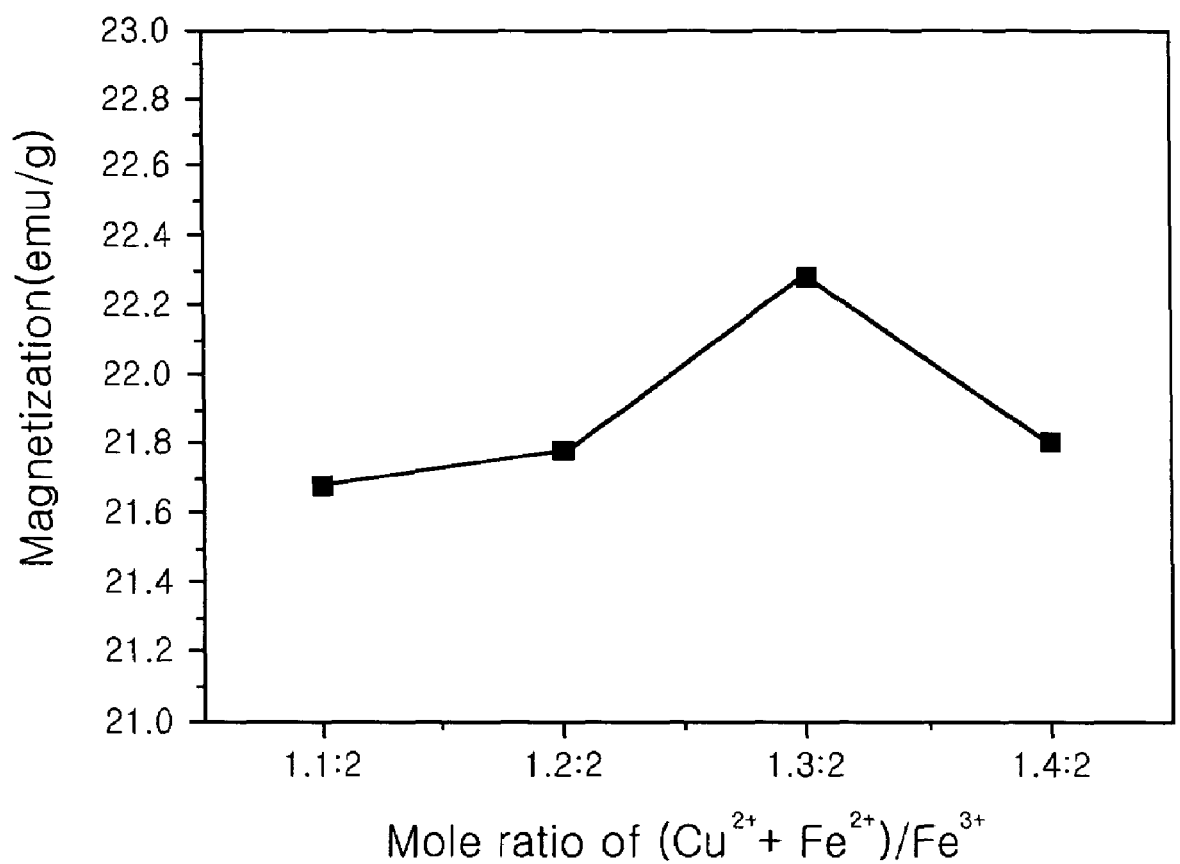
FIG. 6 shows magnetization values of magnetic nanoparticles prepared at various mole ratios of $(Cu^{2+}+Fe^{2+})$ to $Fe^{3+}$.

The results are shown in FIG. 6.

As shown in FIG. 6, the magnetization of the magnetic nanoparticles was maximized at the mole ratio of $(Cu^{2+}+Fe^{2+}):Fe^{3+}=1.3:2$. Also, in the mole ratio of below 1.0:2 or excess 1.4:2, the magnetic nanoparticles could not be obtained.

INDUSTRIAL APPLICABILITY

As described hereinbefore, the radioactive magnetic fluids of the present invention include the component of $Cu^{2+}$ which radiates a β-ray and γ-ray. Since the γ radiation are easily imaged with γ-camera, the magnetic fluids can be gathered to the treatment site with the radiograph under external magnetic field. Therefore, the radioactive magnetic fluids of the present invention can be used for treatment of cancer with no side effect and no damage to normal tissue.

Also, decanoic acid and nonanoic acid as surfactants form tightly bonded monomolecular layers around the magnetic nanoparticles, which are comprised in the radioactive magnetic fluids of the present invention. Such surfactants increase particle-particle repulsion and stability of the magnetic fluids. Also, carboxylic acid of the surfactant is exposed to outside, to prevent the magnetic nanoparticles from being oxidized by air.

What is claimed is:

1. A radioactive magnetic fluid comprising: magnetic nanoparticles of $Cu_xFe_{1-x}O \cdot Fe_2O_3$; and surfactants coated onto the surface of the magnetic nanoparticles, wherein x value is between 0.1 and 0.4 and a component of copper in the magnetic nanoparticles of $Cu_xFe_{1-x}O \cdot Fe_2O_3$ is a radioactive copper.

2. The radioactive magnetic fluids according to claim 1, wherein the magnetic nanoparticles of $Cu_xFe_{1-x}O \cdot Fe_2O_3$ are obtained by coprecipitating components of $Fe^{2+}$ and $Fe^{3+}$ with a component of radioactive $Cu^{2+}$ under presence of a precipitator.

3. The radioactive magnetic fluids according to claim 1, wherein the surfactants comprise a first surfactant coated onto the surface of the magnetic nanoparticles, the first surfactant being decanoic acid, and a second surfactant coated onto the first-coated magnetic nanoparticles, the second surfactant being nonanoic acid.

4. A process for preparing the radioactive magnetic fluids of claim 1, which comprises:
   1) preparing the magnetic nanoparticles of $Cu_xFe_{1-x}O \cdot Fe_2O_3$ by coprecipitating the components of $Fe^{2+}$ and $Fe^{3+}$ with the component of radioactive $Cu^{2+}$ under presence of a precipitator;
   2) first coating the magnetic nanoparticles with decanoic acid; and
   3) second coating the first-coated magnetic nanoparticles with nonanoic acid.

5. The process according to claim 4, wherein the precipitator is sodium hydroxide.

6. The process according to claim 4, wherein the mole ratio of $(Cu^{2+}+Fe^{2+})$ to $Fe^{3+}$ is within range of $(1.1\sim1.4):2$.

7. A therapeutic drug for cancer containing the radioactive magnetic fluid according to claim 1.

8. A diagnostic reagent for cancer containing the radioactive magnetic fluid according to claim 1.

* * * * *